(12) United States Patent
Collins

(10) Patent No.: US 7,867,266 B2
(45) Date of Patent: Jan. 11, 2011

(54) TEMPERATURE MANAGEMENT SYSTEM WITH ASSIST MODE FOR USE WITH HEART-LUNG MACHINE

(75) Inventor: Kenneth A. Collins, Mission Viejo, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 841 days.

(21) Appl. No.: 11/598,352

(22) Filed: Nov. 13, 2006

(65) Prior Publication Data

US 2008/0114430 A1    May 15, 2008

(51) Int. Cl.
*A61F 7/12* (2006.01)
(52) U.S. Cl. .................... 607/105; 607/106
(58) Field of Classification Search ............ 607/105, 607/106
See application file for complete search history.

(56) References Cited

U.S. PATENT DOCUMENTS

| | | | | |
|---|---|---|---|---|
| 5,011,469 A * | 4/1991 | Buckberg et al. | 604/6.11 |
| 5,207,640 A | 5/1993 | Hattler | 604/28 |
| 5,230,862 A | 7/1993 | Berry et al. | 422/48 |
| 5,271,743 A | 12/1993 | Hattler | 604/26 |
| 5,450,516 A | 9/1995 | Pasquali et al. | 385/115 |
| 5,470,659 A | 11/1995 | Baumgart et al. | 428/398 |
| 5,725,949 A | 3/1998 | Pasquail et al. | 428/398 |
| 5,735,809 A | 4/1998 | Gorsuch | 428/364 |
| 5,755,690 A | 5/1998 | Saab | 604/96 |
| 5,837,003 A | 11/1998 | Ginsburg | 607/106 |
| 5,876,667 A | 3/1999 | Gremel et al. | 604/4 |
| 5,879,329 A | 3/1999 | Ginsburg | 604/93 |
| 5,989,238 A | 11/1999 | Ginsburg | 604/93 |
| 6,004,289 A | 12/1999 | Saab | 604/96 |
| 6,019,783 A | 2/2000 | Philips | 607/105 |
| 6,042,559 A | 3/2000 | Dobak | 604/7 |
| 6,096,068 A | 8/2000 | Dobak | 607/105 |
| 6,110,168 A | 8/2000 | Ginsburg | 606/27 |
| 6,126,684 A | 10/2000 | Gobin | 607/113 |
| 6,146,411 A | 11/2000 | Noda | 607/105 |
| 6,149,670 A | 11/2000 | Worthen | 607/3 |
| 6,149,673 A | 11/2000 | Ginsburg | 607/96 |
| 6,149,676 A | 11/2000 | Ginsburg | 607/106 |
| 6,149,677 A | 11/2000 | Dobak | 607/106 |
| 6,165,207 A | 12/2000 | Balding | 607/105 |
| 6,224,624 B1 | 5/2001 | Lasheras | 607/105 |
| 6,231,594 B1 | 5/2001 | Dae | 607/96 |
| 6,231,595 B1 | 5/2001 | Dobak | 607/106 |
| 6,235,048 B1 | 5/2001 | Dobak | 607/104 |
| 6,238,428 B1 | 5/2001 | Werneth | 607/105 |
| 6,245,095 B1 | 6/2001 | Dobak | 607/105 |
| 6,251,129 B1 | 6/2001 | Dobak | 607/105 |
| 6,251,130 B1 | 6/2001 | Dobak | 607/105 |
| 6,254,626 B1 | 7/2001 | Dobak | 607/105 |
| 6,264,679 B1 | 7/2001 | Keller | 607/105 |

(Continued)

OTHER PUBLICATIONS

U.S. Appl. No. 60/272,442, Worthen et al.

*Primary Examiner*—Roy D Gibson
*Assistant Examiner*—Kaitlyn E Helling
(74) *Attorney, Agent, or Firm*—John L. Rogitz

(57) ABSTRACT

A system and method uses both a heart-lung machine (HLM) and a catheter and/or pad to reach a target temperature for, e.g., cardiac bypass surgery. At or about the target temperature, temperature control of the catheter/pad is suspended and patient temperature controlled using only the HLM.

4 Claims, 2 Drawing Sheets

U.S. PATENT DOCUMENTS

| | | | | |
|---|---|---|---|---|
| 6,287,326 | B1 | 9/2001 | Pecor | 607/105 |
| 6,290,717 | B1* | 9/2001 | Philips | 607/113 |
| 6,299,599 | B1* | 10/2001 | Pham et al. | 604/113 |
| 6,306,161 | B1 | 10/2001 | Ginsburg | 607/106 |
| 6,312,452 | B1 | 11/2001 | Dobak | 607/105 |
| 6,325,818 | B1 | 12/2001 | Werneth | 607/105 |
| 6,338,727 | B1 | 1/2002 | Noda | 604/113 |
| 6,364,899 | B1 | 4/2002 | Dobak | 607/113 |
| 6,368,304 | B1 | 4/2002 | Aliberto | 604/113 |
| 6,379,378 | B1 | 4/2002 | Werneth | 607/96 |
| 6,383,210 | B1 | 5/2002 | Magers | 607/105 |
| 6,393,320 | B2 | 5/2002 | Lasersohn | 607/3 |
| 6,405,080 | B1 | 6/2002 | Lasersohn | 607/3 |
| 6,409,747 | B1 | 6/2002 | Gobin | 607/113 |
| 6,416,533 | B1 | 7/2002 | Gobin | 607/113 |
| 6,419,643 | B1 | 7/2002 | Shimada | 600/323 |
| 6,428,563 | B1 | 8/2002 | Keller | 607/105 |
| 6,432,124 | B1 | 8/2002 | Worthen | 607/105 |
| 6,436,130 | B1 | 8/2002 | Philips | 607/105 |
| 6,436,131 | B1 | 8/2002 | Ginsburg | 607/106 |
| 6,440,158 | B1 | 8/2002 | Saab | 604/105 |
| 6,447,474 | B1 | 9/2002 | Balding | 604/66 |
| 6,450,987 | B1 | 9/2002 | Kramer | 604/523 |
| 6,450,990 | B1 | 9/2002 | Walker | 604/113 |
| 6,451,045 | B1 | 9/2002 | Walker | 607/105 |
| 6,454,792 | B1 | 9/2002 | Noda | 607/105 |
| 6,454,793 | B1 | 9/2002 | Evans | 607/105 |
| 6,458,150 | B1 | 10/2002 | Evans | 607/105 |
| 6,460,544 | B1 | 10/2002 | Worthen | 607/105 |
| 6,464,716 | B1 | 10/2002 | Dobak | 607/105 |
| 6,468,296 | B1 | 10/2002 | Dobak | 607/105 |
| 6,471,717 | B1 | 10/2002 | Dobak | 607/105 |
| 6,475,231 | B2 | 11/2002 | Dobak | 607/105 |
| 6,478,811 | B1 | 11/2002 | Dobak | 607/105 |
| 6,478,812 | B2 | 11/2002 | Dobak | 607/105 |
| 6,482,226 | B1 | 11/2002 | Dobak | 607/104 |
| 6,491,039 | B1 | 12/2002 | Dobak | 128/898 |
| 6,491,716 | B2 | 12/2002 | Dobak | 607/105 |
| 6,494,903 | B2 | 12/2002 | Pecor | 607/105 |
| 6,497,721 | B2 | 12/2002 | Ginsburg | 607/106 |
| 6,516,224 | B2 | 2/2003 | Lasersohn | 607/3 |
| 6,517,533 | B1* | 2/2003 | Swaminathan | 606/20 |
| 6,520,933 | B1 | 2/2003 | Evans | 604/103.07 |
| 6,527,798 | B2 | 3/2003 | Ginsburg | 607/106 |
| 6,529,775 | B2 | 3/2003 | Whitebook | 607/100 |
| 6,530,946 | B1 | 3/2003 | Noda | 607/113 |
| 6,533,804 | B2 | 3/2003 | Dobak | 607/105 |
| 6,540,771 | B2 | 4/2003 | Dobak | 607/105 |
| 6,544,282 | B1 | 4/2003 | Dae | 607/105 |
| 6,551,349 | B2 | 4/2003 | Lasheras | 607/105 |
| 6,554,797 | B1 | 4/2003 | Worthen | 604/113 |
| 6,558,412 | B2 | 5/2003 | Dobak | 607/105 |
| 6,572,538 | B2 | 6/2003 | Takase | 600/140 |
| 6,572,638 | B1* | 6/2003 | Dae et al. | 607/96 |
| 6,572,640 | B1* | 6/2003 | Balding et al. | 607/105 |
| 6,576,001 | B2 | 6/2003 | Werneth | 607/96 |
| 6,576,002 | B2 | 6/2003 | Dobak | 607/105 |
| 6,581,403 | B2 | 6/2003 | Whitebook | 62/434 |
| 6,582,398 | B1 | 6/2003 | Worthen | 604/113 |
| 6,582,455 | B1 | 6/2003 | Dobak | 607/105 |
| 6,582,457 | B2 | 6/2003 | Dae | 607/113 |
| 6,585,692 | B1 | 7/2003 | Worthen | 604/113 |
| 6,585,752 | B2 | 7/2003 | Dobak | 607/105 |
| 6,589,271 | B1 | 7/2003 | Tzeng | 607/113 |
| 6,595,967 | B2 | 7/2003 | Kramer | 604/523 |
| 6,599,312 | B2 | 7/2003 | Dobak | 607/105 |
| 6,602,243 | B2 | 8/2003 | Noda | 604/544 |
| 6,602,276 | B2 | 8/2003 | Dobak | 607/105 |
| 6,607,517 | B1 | 8/2003 | Dae | 604/31 |
| 6,610,083 | B2 | 8/2003 | Keller | 607/105 |
| 6,620,130 | B1 | 9/2003 | Ginsburg | 604/113 |
| 6,620,131 | B2 | 9/2003 | Pham | 604/113 |
| 6,620,188 | B1 | 9/2003 | Ginsburg | 607/106 |
| 6,620,189 | B1 | 9/2003 | MacHold | 607/106 |
| 6,623,516 | B2 | 9/2003 | Saab | 607/105 |
| 6,635,076 | B1 | 10/2003 | Ginsburg | 607/106 |
| 6,641,602 | B2 | 11/2003 | Balding | 607/105 |
| 6,641,603 | B2 | 11/2003 | Walker | 607/105 |
| 6,645,234 | B2 | 11/2003 | Evans | 607/113 |
| 6,648,906 | B2 | 11/2003 | Lasheras | 607/105 |
| 6,648,908 | B2 | 11/2003 | Dobak | 607/105 |
| 6,652,565 | B1 | 11/2003 | Shimada | 607/113 |
| 6,656,209 | B1 | 12/2003 | Ginsburg | 607/106 |
| 6,660,028 | B2 | 12/2003 | Magers | 607/105 |
| 6,673,098 | B1 | 1/2004 | MacHold | 607/106 |
| 6,676,688 | B2 | 1/2004 | Dobak | 607/105 |
| 6,676,689 | B2 | 1/2004 | Dobak | 607/105 |
| 6,676,690 | B2 | 1/2004 | Werneth | 607/105 |
| 6,679,906 | B2* | 1/2004 | Hammack et al. | 607/105 |
| 6,679,907 | B2 | 1/2004 | Dobak | 607/105 |
| 6,682,551 | B1 | 1/2004 | Worthen | 607/105 |
| 6,685,732 | B2 | 2/2004 | Kramer | 607/106 |
| 6,685,733 | B1 | 2/2004 | Dae | 607/105 |
| 6,692,488 | B2 | 2/2004 | Dobak | 606/21 |
| 6,692,519 | B1 | 2/2004 | Hayes | 607/105 |
| 6,695,873 | B2 | 2/2004 | Dobak | 607/105 |
| 6,695,874 | B2 | 2/2004 | MacHold | 607/106 |
| 6,699,268 | B2 | 3/2004 | Kordis | 607/113 |
| 6,702,783 | B1 | 3/2004 | Dae | 604/113 |
| 6,702,839 | B1 | 3/2004 | Dae | 607/96 |
| 6,702,840 | B2 | 3/2004 | Keller | 607/105 |
| 6,702,841 | B2 | 3/2004 | Nest | 607/105 |
| 6,702,842 | B2 | 3/2004 | Dobak | 607/105 |
| 6,706,060 | B2 | 3/2004 | Tzeng | 607/105 |
| 6,709,448 | B2 | 3/2004 | Walker | 607/105 |
| 6,716,188 | B2 | 4/2004 | Noda | 604/6.13 |
| 6,716,236 | B1 | 4/2004 | Tzeng | 607/113 |
| 6,719,723 | B2 | 4/2004 | Werneth | 604/113 |
| 6,719,724 | B1 | 4/2004 | Walker | 604/113 |
| 6,719,779 | B2 | 4/2004 | Daoud | 607/105 |
| 6,726,653 | B2 | 4/2004 | Noda | 604/113 |
| 6,726,708 | B2 | 4/2004 | Lasheras | 607/105 |
| 6,726,710 | B2 | 4/2004 | Worthen | 607/105 |
| 6,733,517 | B1 | 5/2004 | Collins | 607/105 |
| 6,740,109 | B2 | 5/2004 | Dobak | 607/105 |
| 6,749,585 | B2 | 6/2004 | Aliberto | 604/113 |
| 6,749,625 | B2 | 6/2004 | Pompa | 607/105 |
| 6,752,786 | B2 | 6/2004 | Callister | 604/113 |
| 6,755,850 | B2 | 6/2004 | Dobak | 607/104 |
| 6,755,851 | B2 | 6/2004 | Noda | 607/113 |
| 6,924,467 | B2 | 8/2005 | Ellis et al. | |
| 7,077,825 | B1* | 7/2006 | Stull | 604/113 |
| 2001/0007951 | A1 | 7/2001 | Dobak | 607/106 |
| 2001/0016764 | A1 | 8/2001 | Dobak, III | 607/105 |
| 2001/0041923 | A1 | 11/2001 | Dobak | 607/105 |
| 2002/0007203 | A1 | 1/2002 | Gilmartin | 607/105 |
| 2002/0016621 | A1 | 2/2002 | Werneth | 607/96 |
| 2002/0026227 | A1* | 2/2002 | Philips | 607/113 |
| 2002/0068964 | A1 | 6/2002 | Dobak | 607/113 |
| 2002/0077680 | A1 | 6/2002 | Noda | 600/549 |
| 2002/0091429 | A1 | 7/2002 | Dobak | 607/105 |
| 2002/0111616 | A1 | 8/2002 | Dea | 606/27 |
| 2002/0151946 | A1 | 10/2002 | Dobak, III | 607/105 |
| 2002/0177804 | A1 | 11/2002 | Saab | 607/105 |
| 2002/0183692 | A1 | 12/2002 | Callister | 604/113 |
| 2002/0193738 | A1 | 12/2002 | Adzich | 604/113 |
| 2002/0193853 | A1 | 12/2002 | Worthen | 607/3 |
| 2002/0193854 | A1 | 12/2002 | Dobak | 607/105 |
| 2003/0074038 | A1* | 4/2003 | Gruszecki et al. | 607/104 |
| 2003/0078640 | A1* | 4/2003 | Carson et al. | 607/104 |
| 2003/0078641 | A1 | 4/2003 | Dobak | 607/105 |
| 2003/0114835 | A1 | 6/2003 | Noda | 604/544 |
| 2003/0114903 | A1* | 6/2003 | Ellingboe | 607/104 |
| 2003/0135252 | A1* | 7/2003 | MacHold et al. | 607/106 |

| | | | | | | |
|---|---|---|---|---|---|---|
| 2003/0144714 A1 | 7/2003 | Dobak | 607/104 | 2004/0073280 A1 | 4/2004 | Dae |
| 2003/0187489 A1 | 10/2003 | Dobak | 607/105 | 2004/0087934 A1 | 5/2004 | Dobak |
| 2003/0195465 A1 | 10/2003 | Worthen | 604/113 | 2004/0102825 A1 | 5/2004 | Daoud |
| 2003/0195466 A1 | 10/2003 | Pham | 604/113 | 2004/0102826 A1 | 5/2004 | Lasheras |
| 2003/0195597 A1 | 10/2003 | Keller | 607/105 | 2004/0102827 A1 | 5/2004 | Werneth |
| 2003/0216799 A1 | 11/2003 | Worthen | 606/27 | 2004/0106969 A1 | 6/2004 | Dobak |
| 2003/0225336 A1 | 12/2003 | Callister | 600/505 | 2004/0111138 A1 | 6/2004 | Bleam ... 607/105 |
| 2004/0034399 A1 | 2/2004 | Ginsburg | 607/106 | 2004/0116987 A1 | 6/2004 | Magers |
| 2004/0039431 A1 | 2/2004 | Machold | | 2004/0116988 A1 | 6/2004 | Hammack |
| 2004/0044388 A1 | 3/2004 | Pham | 607/105 | 2004/0127851 A1 | 7/2004 | Noda ... 604/503 |
| 2004/0050154 A1 | 3/2004 | Machold | | 2004/0195178 A1 | 10/2004 | Carpenter et al. |
| 2004/0054325 A1 | 3/2004 | Ginsburg | 604/113 | | | |

\* cited by examiner

TEMPERATURE MANAGEMENT SYSTEM WITH ASSIST MODE FOR USE WITH HEART-LUNG MACHINE

FIELD OF THE INVENTION

The present invention relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present invention, the above-mentioned advantages in regulating temperature can be realized by cooling or heating the patient's entire body. Moreover, the present invention understands that since many patients already are intubated with central venous catheters for other clinically approved purposes anyway such as drug delivery and blood monitoring, providing a central venous catheter that can also cool or heat the blood requires no additional surgical procedures for those patients. The following U.S. patents, all of which are incorporated herein by reference, disclose various intravascular catheters/systems/methods: U.S. Pat. Nos. 6,749,625, 6,786,916, 6,581,403, 6,454,792, 6,436,130, 6,146,411, 6,109,783, 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, and U.S. patent application Ser. No. 10/355,776. Less optimally, surface cooling can be used. U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference, disclose such surface cooling systems. In both intravascular catheters and external pad systems, coolant such as a gas or saline is circulated through the heat exchange element.

Regardless of the particular heat exchange element that is engaged with the patient, as understood herein it may be advantageous to use such a system during surgical procedures to control patient temperature. As further understood herein, some procedures may employ another component such as a heart-lung machine (HLM) that can also function to control patient temperature. The present invention understands that during such procedures, a primary temperature control system such as those disclosed in the above patents can be used to assist the other component, e.g., the HLM, in reducing patient temperature to a very low level. However, as further recognized herein it is important to avoid the control processor of one system from "fighting" the control processor of the other system during such assist procedures.

SUMMARY OF THE INVENTION

A method includes engaging a heat exchange element with a patient. The heat exchange element is coupled to a primary control system for controlling patient temperature. The method also includes engaging a component such as a heart lung machine (HLM) with the patient for, e.g., cardiac bypass surgery, with the component also controlling patient temperature. The primary control system is used to assist the component in establishing a target patient temperature. Then, at or about target temperature being reached, temperature control functions of the primary control system are suspended so that only the component controls patient temperature.

The heat exchange element can include an intravascular catheter and/or a pad applied externally to a patient's skin.

In another aspect, a system for exchanging heat with primary coolant flowing through a patient-engageable heat exchange element includes a processor executing logic including receiving a target temperature signal, and resetting a low temperature alarm setpoint based on the target temperature signal.

In still another aspect, a method includes engaging a heart-lung machine (HLM) with a patient and engaging a heat exchange element that is not part of the HLM with the patient. The method further includes using both the HLM and heat exchange element to approach a target patient temperature. The method also includes at or about the target temperature, suspending temperature control of the heat exchange element and controlling patient temperature using only the HLM.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
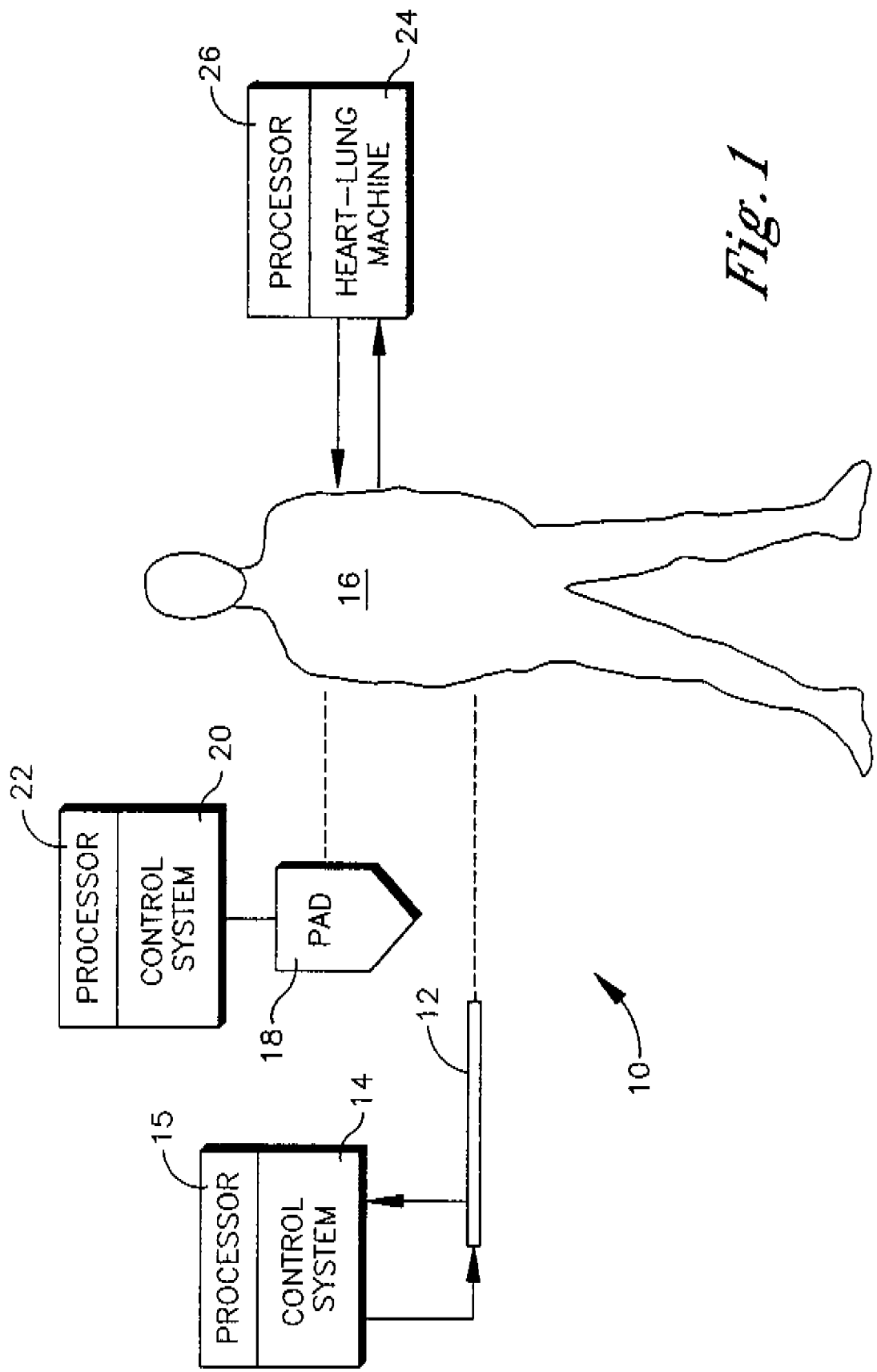
FIG. 1 is a schematic diagram showing two heat exchange modalities for use of one or both as "primary" temperature control systems that may be used to assist another component, such as a HLM, in controlling patient temperature.

Referring initially to FIG. 1, a system is shown, generally designated 10, that may include a heat exchange catheter 12 that is in fluid communication with a catheter temperature control system 14 that includes a processor 15 executing logic described in one or more of the patents referenced herein and also described further below in reference to FIG. 2.

In accordance with present principles, the system 10 can be used to induce therapeutic hypothermia in a patient 16 using a catheter in which coolant such as but not limited to saline circulates in a closed loop, such that no coolant enters the body. While certain preferred catheters are disclosed below, it is to be understood that other catheters can be used in accordance with present principles, including, without limitation, any of the catheters disclosed in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684. The catheter 12 may be placed in the venous system, e.g., in the superior or inferior vena cava. Examples of non-limiting control systems 14 are shown in U.S. Pat. Nos. 6,786,916, 6,581,403, 6,454,792, 6,436,130, 6,146,411, and 6,109,783, incorporated herein by reference.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by a pad controller 20 with processor 22 in accordance with principles set forth in the external pad patents to exchange heat with the patient 16, including to induce therapeutic mild (32° C.-35° C.) or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The control systems 14, 20 may be implemented by a single system having one or more processors for executing temperature control algorithms in accordance with the referenced patents.

One or both of the primary control systems 14, 20 may be used during, e.g., a surgical procedure such as cardiac bypass surgery that might employ a component such as but not limited to a heart-lung machine (HLM) 24 with component processor 26 that happens to control blood temperature extracorporeally, in addition to other functions it might perform such as blood oxygenation. During some of these procedures it might happen to be desirable to cool the patient to temperatures (e.g., fifteen degrees Centigrade) far lower than those normally used for therapeutic hypothermia (e.g., mild hypothermia temperatures). As recognized herein, one or both of the primary control systems 14, 20 can be used to assist the HLM 24 in lowering patient temperature. It should be understood that while for simplicity the discussion below relates to using only the primary control system 14 with catheter 12 to assist the HLM 24, one or both of the primary control systems 14, 20 can be used to assist the HLM 24.

Figure 2:
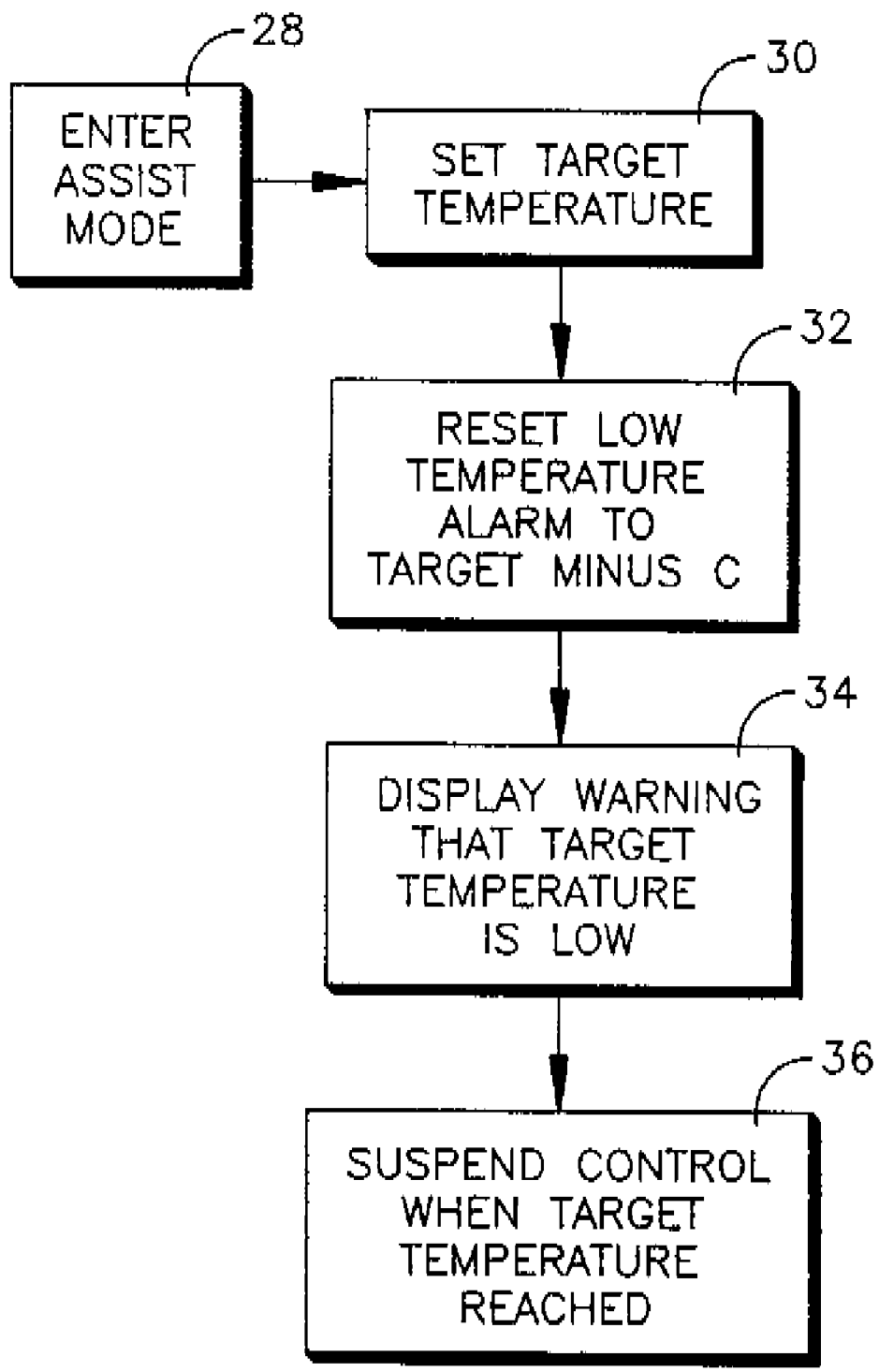
FIG. 2 is a flow chart of the present logic.

Now referring to FIG. 2, at block 28 a user manipulates controls on the primary system 14 to cause the system 14 to enter the assist mode, in which target temperature is set at block 30. Because target temperature in procedures that might require very low patient temperatures, the low temperature alarm of the system 14, normally set around thirty two degrees C. or so, is reset at block 32 to be "C" degrees (e.g., two) below the target temperature set at block 30. Consistent with the reset of the low temperature alarm setpoint, a warning can be displayed on the system 14 at block 34 to the effect that patient health can be compromised at such low temperatures. Once target temperature is substantially reached, to avoid the primary control system processor 22 counteracting the temperature control efforts of the HLM processor 26, at block 36 the temperature control functions of the primary system processor 22 are suspended, so that only the HLM 24 controls patient temperature once target temperature is reached.

While the particular TEMPERATURE MANAGEMENT SYSTEM WITH ASSIST MODE FOR USE WITH HEART-LUNG MACHINE is herein shown and described in detail, it is to be understood that the subject matter which is encompassed by the present invention is limited only by the claims.

What is claimed is:

1. A system for exchanging heat with primary coolant flowing through a patient-engageable heat exchange element, the system having a nominal low temperature alarm setpoint that is substantially at a low end of a temperature range of mild hypothermia, the system comprising:
    a processor executing logic comprising:
        determining that the system is in an assist mode for assisting another component in reducing patient temperature;
        receiving a target temperature signal representing a temperature below the nominal low temperature alarm setpoint; and
        resetting the low temperature alarm setpoint to be below the target temperature signal responsive to a determination that the system is in the assist mode.

2. The system of claim 1, wherein the logic executed by the processor further comprises:
    establishing primary coolant temperature to approach a target temperature indicated by the target temperature signal; and
    at or about target temperature, suspending control of primary coolant temperature.

3. The system of claim 1, wherein the heat exchange element is an intravascular catheter.

4. A Method comprising:
    engaging an intravascular heat exchange catheter with the vasculature of a patient receiving treatment from a heart-lung machine;
    controlling temperature of working fluid through the heat exchange catheter by using a heat exchange system having a low temperature alarm setpoint of around thirty two degrees C.;
    selecting an assist mode of the heat exchange system wherein the heat exchange system assists the heart-lung machine to reduce patient temperature;
    receiving a target temperature below the low temperature alarm setpoint;
    responsive to receiving the target temperature and to a determination that the system is in the "assist" mode, resetting the low temperature alarm setpoint to a value below the target temperature.

\* \* \* \* \*